US006730487B2

(12) United States Patent
Latov et al.

(10) Patent No.: US 6,730,487 B2
(45) Date of Patent: May 4, 2004

(54) SURFACE PLASMON RESONANCE BIOSENSOR FOR MEASUREMENT OF ANTI-GLYCOLIPID ANTIBODY LEVELS IN NEUROPATHY

(75) Inventors: Norman Latov, Irvington, NY (US); Armin Alaedini, New York, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 147 days.

(21) Appl. No.: 09/825,572

(22) Filed: Apr. 3, 2001

(65) Prior Publication Data

US 2002/0177161 A1 Nov. 28, 2002

(51) Int. Cl.$^7$ ............................................... G01N 33/53
(52) U.S. Cl. ........................ 435/7.1; 385/12; 385/129; 385/130; 356/418; 422/82.11; 436/164; 436/165; 436/518; 436/524; 436/525; 436/805
(58) Field of Search ................................ 436/518, 524, 436/527, 164, 165, 172, 805, 525; 435/7.1; 356/418; 422/82.11; 385/12, 129, 130

(56) References Cited

U.S. PATENT DOCUMENTS 5,492,840 A * 2/1996 Malmqvist et al. ......... 436/518

OTHER PUBLICATIONS

Catimel, B et al., (1998) Direct immobilization of gangliosides onto gold–carboxymethyldextran sensor surfaces by hydrophobic interaction: applications to antibody characterization, *Glycobiology* 8: 927–938.

Harrison, Blair A et al., (1997) A kinetics approach to the characterization of an IgM specific for the glycolipid asialo–GM1, *Journal of Immunological Methods* 212: 29–39.

Malmqvist M. Biacore: an affinity biosensor system for characterization of biomolecular interactions. Biochem Soc Trans 1999; 27:335–340; and.

Fagerstam LG, Forstell–Karlsson A, Karlsson R, Presson B, Ronberg I. Biospecific interaction analysis using surface plasmon resonance detection applied to kinetic, binding site and concentration analysis. J Chromatography 1992; 597: 397–410.

* cited by examiner

*Primary Examiner*—Christopher L. Chin
(74) *Attorney, Agent, or Firm*—John P. White; Cooper and Dunham LLP (57) ABSTRACT

The present invention provides a method of detecting human antibodies in a sera solution. The invention also provides a method of quantitating anti-glycolipid antibody levels in solutions. The invention provides a method of diagnosing disease states, including neurological diseases, by quantitating a subject's antibody levels.

12 Claims, 6 Drawing Sheets

SURFACE PLASMON RESONANCE BIOSENSOR FOR MEASUREMENT OF ANTI-GLYCOLIPID ANTIBODY LEVELS IN NEUROPATHY

BACKGROUND

Elevated titers of anti-GM1 ganglioside antibodies (anti-GM1) are associated with multifocal motor neuropathy, lower motor neuron disease syndromes, and with the acute motor axonal neuropathy variant of the Guillian-Barré syndrome.[1-5] Assays for anti-GM1 antibodies are routinely used in clinical practice to aid in the evaluation of patients suspected of having these syndromes.

Anti-GM1 antibodies are typically measured using the ELISA system, in which increasing serum dilutions are tested for binding to GM1-coated microwells.[6] However, the assay takes several days to perform, is costly, and is done at non-physiologic conditions of temperature and antibody concentration. Issues of methodology have also limited the usefulness of the technique.[7-10] There is a need for a faster and more reliable test to detect and measure anti-GM1 antibodies.

Here we disclose a novel method for the rapid detection and quantitation of serum antibodies in serum. In the invention disclosed here we present data showing quantitation of serum anti-ganglioside antibodies in serum. The system utilizes a surface plasmon resonance-based optical biosensor. Gangliosides are immobilized on the surface of a sensor chip comprised of a carboxymethyl dextran layer linked to a thin gold film coated on a glass slide. The sensor chip is brought in contact with a flow cell carrying the analyte. Applying the phenomenon of surface plasmon resonance, possible interactions between the analyte in the flow cell and the gangliosides, leading to changes in the refractive index at the surface of the chip, can be followed.[11,12] The binding of anti-GM1 antibodies in a sample to immobilized GM1 can be observed in real time without the use of secondary labels. The invention disclosed here reveals a method of diagnosing human diseases by detection and quantitation of antibodies in human sera.

SUMMARY OF THE INVENTION

The present invention provides a method of detecting antibodies in a solution comprising:
  a) contacting the solution with an antigen-coated surface of a sensor chip under conditions that permit anti-antigen antibodies to bind to the antigen coating;
  b) detecting the change in surface plasmon resonance signal of the sensor chip resulting from the anti-antigen antibodies binding to the antigen coating.

The present invention provides a method of detecting antibodies as described hereinabove, wherein the antigen is a glycolipid.

The present invention provides a method of detecting antibodies as described hereinabove wherein the anti-antigen antibodies are anti-glycolipid antibodies.

The present invention provides a method of detecting antibodies as described hereinabove wherein the antigen is a ganglioside and the anti-antigen antibodies are anti-ganglioside antibodies.

The present invention provides a method of detecting anti-glycolipid antibodies in a solution wherein the solution contains anti-glycolipid antibodies that bind to the glycolipid-coated surface of the sensor chip and alter the surface plasmon resonance.

The present invention provides a method of detecting anti-glycolipid antibodies in a solution as described hereinabove, wherein the glycolipid is a ganglioside and wherein a control surface plasmon resonance value is subtracted from the surface plasmon resonance signal.

The present invention provides a method of detecting anti-glycolipid antibodies in a solution as described hereinabove, wherein the control surface plasmon resonance value comprises the signal detected from the surface of the sensor chip coated with a control antigen, wherein the chip is also alternatively exposed to the solution being evaluated for anti-glycolipid antibodies. The present invention also provides a method wherein the control antigen is ganglioside GM2. The present invention also provides a method wherein the anti-antigen antibody is anti-ganglioside GM1 antibody.

The present invention provides a method of detecting anti-glycolipid antibodies in a solution as described hereinabove, wherein the surface plasmon resonance signal is detected using an optical detector.

The present invention provides a method of detecting anti-glycolipid antibodies in a solution as described hereinabove, wherein the solution is human blood or a derivative of human blood.

The present invention provides a method of detecting anti-glycolipid antibodies in a solution as described hereinabove, wherein the solution is human sera.

The present invention provides a method of detecting anti-glycolipid antibodies in a solution as described hereinabove, wherein the anti-glycolipid antibody is an anti-glycolipid Immunoglobulin G.

The present invention provides a method of detecting anti-glycolipid antibodies in a solution as described hereinabove, wherein the anti-glycolipid antibody is an anti-glycolipid Immunoglobulin M.

The present invention provides a method of detecting anti-glycolipid antibodies in a solution as described hereinabove, wherein the anti-glycolipid antibody is an anti-ganglioside antibody.

The present invention provides a method of detecting anti-glycolipid antibodies in a solution as described hereinabove, wherein the anti-glycolipid antibody is human.

The present invention provides a method of determining the anti-glycolipid antibody isotype present in the solution comprising the methods described hereinabove, wherein the tested solution is washed from the surface of the sensor chip and a second solution containing a secondary antibody is introduced to the surface.

The present invention provides a method of increasing the optical signal size of the methods described hereinabove, comprising washing the tested solution from the surface of the sensor chip and applying the second solution containing the secondary antibody to the surface.

The present invention provides a method of detecting anti-glycolipid antibodies in a solution as described hereinabove, wherein the secondary antibody is an anti-Immunoglobulin G.

The present invention provides a method of detecting anti-glycolipid antibodies in a solution as described hereinabove, wherein the secondary antibody is an anti-Immunoglobulin M.

The present invention provides the use of the methods described hereinabove in diagnosing a disease in a subject.

The present invention provides the use of the methods described hereinabove in diagnosing a neurological disease in a subject.

The present invention provides the use of the methods described hereinabove in quantitating levels of anti-antigen antibodies in a subject.

The present invention provides the use of the method described hereinabove in evaluating a neuropathic disease in a subject, wherein the disease is Guillian-Barré syndrome, motor neuropathy, peripheral neuropathy or autoimmune neuropathy.

BRIEF DESCRIPTION OF THE FIGURES

FIGS. 2A and 2B. Presence of anti-GM1 antibodies in serum is detected and visualized in the form of sensorgrams. (A) Two sensorgrams result from the interaction of sample with the GM1- and GM2-coated surfaces of the sensor chip. (B) Subtraction of response for the control flow cell from response for GM1-coated flow cell results in a corrected sensorgram indicating net binding of anti-GM1 antibodies. Final measurement of response difference is taken at 20 seconds after the end of injection. S=Start of injection, E=End of injection.

FIG. 3. Use of a secondary antibody for signal enhancement. (A) Injection of a 1:100,000 dilution of an MMN serum sample with anti-GM1 antibodies. (B) Introduction of a 0.5 mg/mL solution of goat anti-human IgM following sample injection, enhanced the signal nearly six fold.

FIGS. 4A and 4B. Use of secondary antibodies for identification of the anti-GM1 autoantibody isotype. (A) Analysis of a serum sample from an MMN patient with anti-IgM and anti-IgG antibodies indicated that the antibodies in the serum are of the IgM class. (B) Similar analysis of a sample from a GBS patient indicated the presence of IgG class antibodies.

DETAILED DESCRIPTION OF THE INVENTION

The following definitions are presented as an aid in understanding this invention:

ALS - Amyotrophic Lateral Sclerosis;
CIDP - Chronic Inflammatory Demyelinating Polyneuropathy;
ELISA - Enzyme-linked Immunosorbent Assay;
GBS - Guillian-Barré syndrome;
GM1 - Ganglioside $G_{M1}$;
GM2 - Ganglioside $G_{M2}$;
IgG - Immunoglobulin G;
IgM - Immunoglobulin M;
MAG - Myelin Associated Glycoprotein;
MMN - Multifocal Motor Neuropathy;
SPR - Surface Plasmon Resonance.

Having due regard to the preceding definitions, the present invention provides a method of detecting antibodies in a solution comprising:

a) contacting the solution with an antigen-coated surface of a sensor chip under conditions that permit anti-antigen antibodies to bind to the antigen coating;

b) detecting the change in surface plasmon resonance signal of the sensor chip resulting from the anti-antigen antibodies binding to the antigen coating.

In one embodiment the antigen coated surface is a glycolipid-coated surface. In one embodiment the antigen coated surface is a protein coated surface. In one embodiment the surface coated with ganglioside GM1. In another embodiment the glycolipid-coated surface is coated with ganglioside GM2. In one embodiment the solution being tested is human sera. In another embodiment the antibodies being detected are human antibodies. In one embodiment the surface plasmon resonance signal is detected by an optical detection apparatus. In one embodiment the binding of antibodies to the antigen surface causes a change in the surface plasmon resonance signal. In one embodiment the antigen is coated onto the surface of the chip using any common means including, but not limited to, covalent linking and conjugation.

The present invention provides a method of detecting antibodies as described hereinabove, wherein the antigen is a glycolipid.

The present invention provides a method of detecting antibodies as described hereinabove wherein the anti-antigen antibodies are anti-glycolipid antibodies.

The present invention provides a method of detecting antibodies as described hereinabove wherein the antigen is a ganglioside and the anti-antigen antibodies are anti-ganglioside antibodies.

The present invention provides a method of detecting anti-glycolipid antibodies in a solution wherein the solution contains anti-glycolipid antibodies that bind to the glycolipid-coated surface of the sensor chip and alter the surface plasmon resonance. In one embodiment the anti-glycolipid antibodies are anti-ganglioside GM1 antibodies. In one embodiment the glycolipid-coated surface is a ganglioside GM1-coated surface.

The present invention provides a method of detecting anti-glycolipid antibodies in a solution as described hereinabove, wherein the glycolipid is a ganglioside and wherein a control surface plasmon resonance value is subtracted from the surface plasmon resonance signal. In one embodiment the surface plasmon resonance signal is detected by an optical detection apparatus. In one embodiment the control surface plasmon resonance value is measured when the surface of the sensor chip is coated with a control antigen.

The present invention provides a method of detecting anti-glycolipid antibodies in a solution as described hereinabove, wherein the control surface plasmon resonance value comprises the signal detected from the surface of the sensor chip coated with a control antigen, wherein the chip is also alternatively exposed to the solution being evaluated for anti-glycolipid antibodies. The present invention also provides a method wherein the control antigen is ganglioside GM2. The present invention also provides a method wherein the anti-antigen antibody is anti-ganglioside GM1 antibody.

The present invention provides a method of detecting anti-glycolipid antibodies in a solution as described hereinabove, wherein the surface plasmon resonance signal is detected using an optical detector. In one embodiment the binding of anti-glycolipid antibodies to the glycolipid-coated surface of a sensor chip alters the refractive index of the surface and thus alters the optical signal detected.

The present invention provides a method of detecting anti-glycolipid antibodies in a solution as described hereinabove, wherein the solution is human blood or a derivative of human blood. Derivative of human blood includes, but is not limited to, centrifuged blood products and sera.

The present invention provides a method of detecting anti-glycolipid antibodies in a solution as described hereinabove, wherein the solution is human sera. Human sera includes sera derivatives or modified sera as well as plain sera.

The present invention provides a method of detecting anti-glycolipid antibodies in a solution as described hereinabove, wherein the anti-glycolipid antibody is an anti-glycolipid Immunoglobulin G.

The present invention provides a method of detecting anti-glycolipid antibodies in a solution as described hereinabove, wherein the anti-glycolipid antibody is an anti-glycolipid Immunoglobulin M.

The present invention provides a method of detecting anti-glycolipid antibodies in a solution as described hereinabove, wherein the anti-glycolipid antibody is an anti-ganglioside antibody. In one embodiment the anti-glycolipid antibody is an anti-ganglioside GM1 antibody.

The present invention provides a method of detecting anti-glycolipid antibodies in a solution as described hereinabove, wherein the anti-glycolipid antibody is human. In one embodiment the anti-glycolipid antibody is a human anti-ganglioside GM1 antibody.

The present invention provides a method of determining the anti-glycolipid antibody isotype present in the solution comprising the methods described hereinabove, wherein the tested solution is washed from the surface of the sensor chip and a second solution containing a secondary antibody is introduced to the surface. In one embodiment the sensor chip surface is spatially separated into two distinct areas, one coated with the test antigen and the other coated with the control antigen. In one embodiment the antibody being quantitated binds to the test antigen. Quantitating the test antibody level means comparing the change in surface plasmon resonance signal seen when the test solution is introduced to the test antigen coated surface to the change in control surface plasmon resonance signal seen when the test solution is introduced to the control antigen coated surface. The test antibody is the antibody being tested for by the method, i.e. the antibody that can bind to the antigen-coated surface of the sensor chip.

The present invention provides a method of increasing the optical signal size of the methods described hereinabove, comprising washing the tested solution from the surface of the sensor chip and applying the second solution containing the secondary antibody to the surface. In one embodiment the secondary antibody binds to test antibody which in turn is bound to the antigen-coated surface of the sensor chip. In one embodiment the secondary antibody bound to the test antibody which in turn is bound to the antigen-coated surface of the sensor chip provides a bigger change in surface plasmon resonance signal than the test antibody alone bound to the antigen-coated surface of the sensor chip.

The present invention provides a method of detecting anti-glycolipid antibodies in a solution as described hereinabove, wherein the secondary antibody is an anti-Immunoglobulin G.

The present invention provides a method of detecting anti-glycolipid antibodies in a solution as described hereinabove, wherein the secondary antibody is an anti-Immunoglobulin M.

The present invention provides the use of the methods described hereinabove in diagnosing a disease in a subject. Diagnosing a disease means identifying that disease state in a subject. In one embodiment the disease is diagnosed by quantitating the levels of an antibody in a subject. In a further embodiment the antibody is a characteristic of the disease state. In another embodiment an antibody level in the subject is a characteristic of the disease state.

The present invention provides the use of the methods described hereinabove in diagnosing a neurological disease in a subject.

The present invention provides the use of the methods described hereinabove in quantitating levels of anti-antigen antibodies in a subject. In one embodiment the quantitation of levels of anti-antigen antibodies in a subject is used for assessing the success of treating the disease in a subject.

The present invention provides the use of the method described hereinabove in evaluating a neuropathic disease in a subject, wherein the disease is Guillian-Barré syndrome, motor neuropathy, peripheral neuropathy or autoimmune neuropathy. In one embodiment the presence of human anti-glycolipid antibodies in the test solution is used as an indicator in diagnosing the diseases mentioned hereinabove.

Experimental Results

Sera from a total of 26 individuals were examined for anti-GM1 antibodies by surface plasmon resonance biosensor assay and ELISA. Of the eight sera examined from MMN patients, five tested positive for anti-GM1 antibodies by the SPR assay, while four were positive by ELISA. Of the two sera examined from GBS patients, one was positive for anti-GM1 antibodies by both assays. All sera from patients with CIDP, ALS, demyelinating neuropathy associated with anti-MAG antibodies, and Miller Fisher variant of GBS, as well as those from normal subjects tested negative for anti-GM1 antibodies by SPR biosensor assay and ELISA (table 1).

Figure 3:
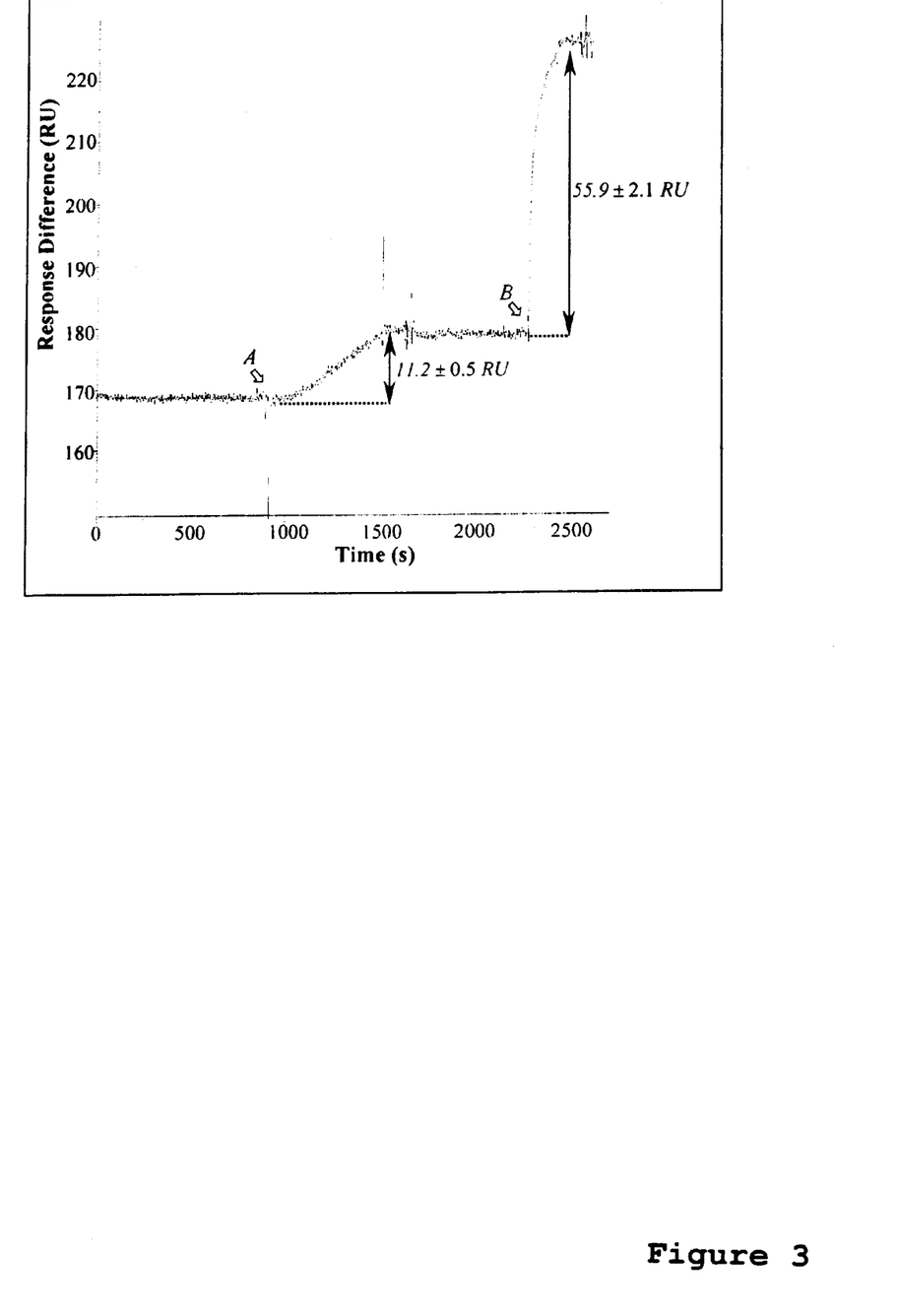

Signal enhancement was studied by analysis of a sample with anti-GM1 antibody titer of 51,200, as determined by ELISA. Detection of anti-GM1 antibody in the sample was possible with at least 100,000 fold dilution using the biosensor. Signal due to interaction of antibody with the antigen-coated sensor chip was enhanced by increasing sample contact time with the chip, either by using a higher sample volume or by decreasing the flow rate. A dramatic enhancement of sensorgram response, however, was possible with the aid of a secondary antibody. While a 100,000 fold dilution of the sample yielded a response of 11.2±0.5 RU, injection of a 0.5 mg/mL solution of goat anti-human IgM (25 $\mu$L at 10 $\mu$L/min) following sample injection (100 $\mu$L at 10 $\mu$L/min), increased the response by 55.9±2.1 RU (FIG. 3).

Secondary antibodies were also utilized as a tool for identifying the anti-ganglioside immunoglobulin isotype. To demonstrate their use, 0.1 mg/mL solutions of goat anti-human IgM or anti-human IgG were injected (25 $\mu$L at 25 $\mu$L/min), following injections of 1:40 dilution of a serum sample from a representative patient (no. 2) with MMN (FIG. 4A). As expected, only anti-IgM antibodies demonstrated binding to the sensor chip surface, resulting in an increase in response, and indicating the presence of IgM anti-GM1 antibodies in sample. This procedure was repeated for a serum from a patient with Guillian-Barré syndrome and antibodies against GM1. Only anti-IgG antibodies showed binding, demonstrating the presence of IgG class anti-GM1 antibodies in this sample (FIG. 4B).

Figure 5:
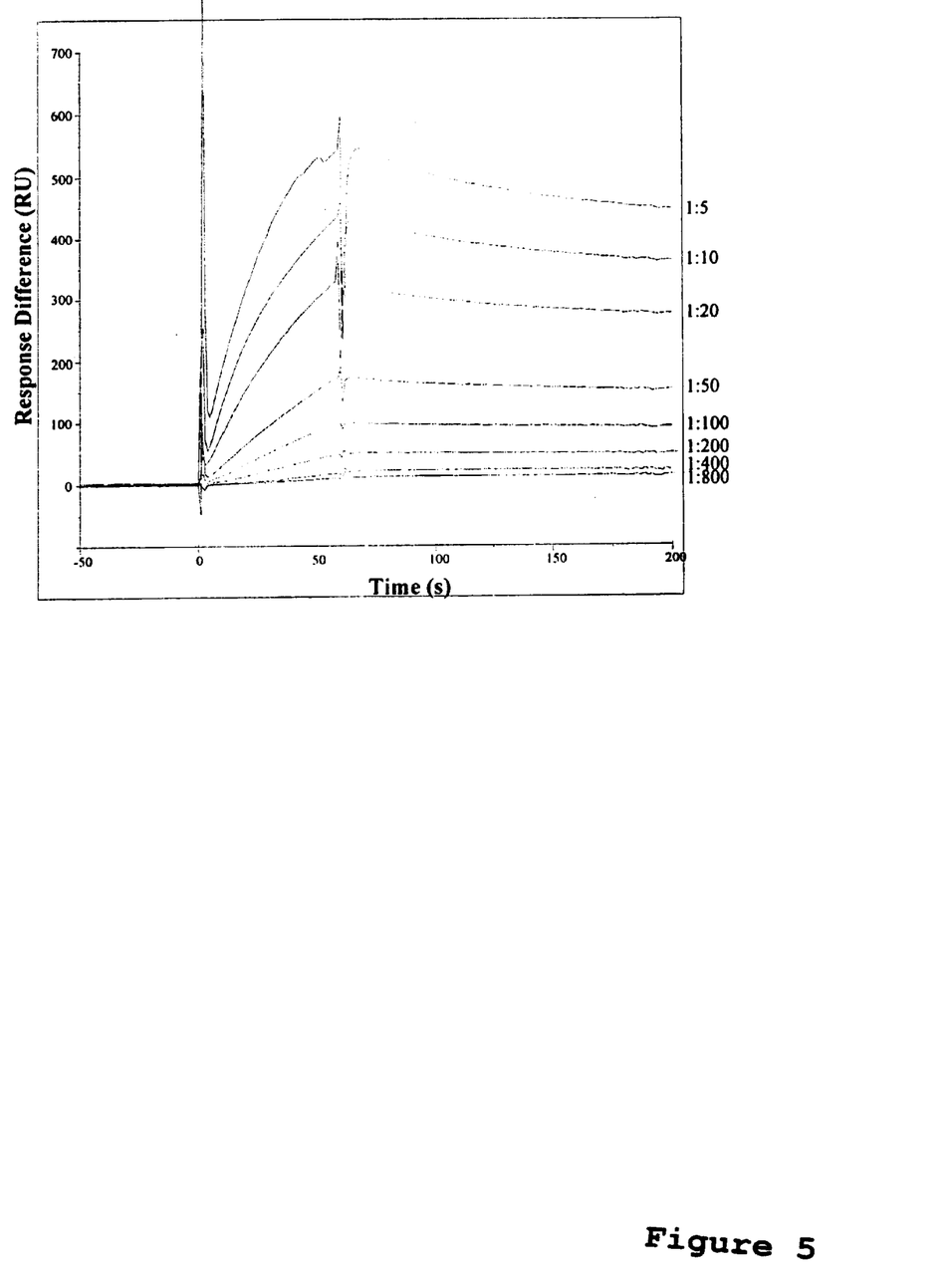
FIG. 5. Corrected sensorgrams for a serially diluted serum sample (1:5 to 1:800) from a representative MMN patient with anti-GM1 antibodies.
Figure 6:
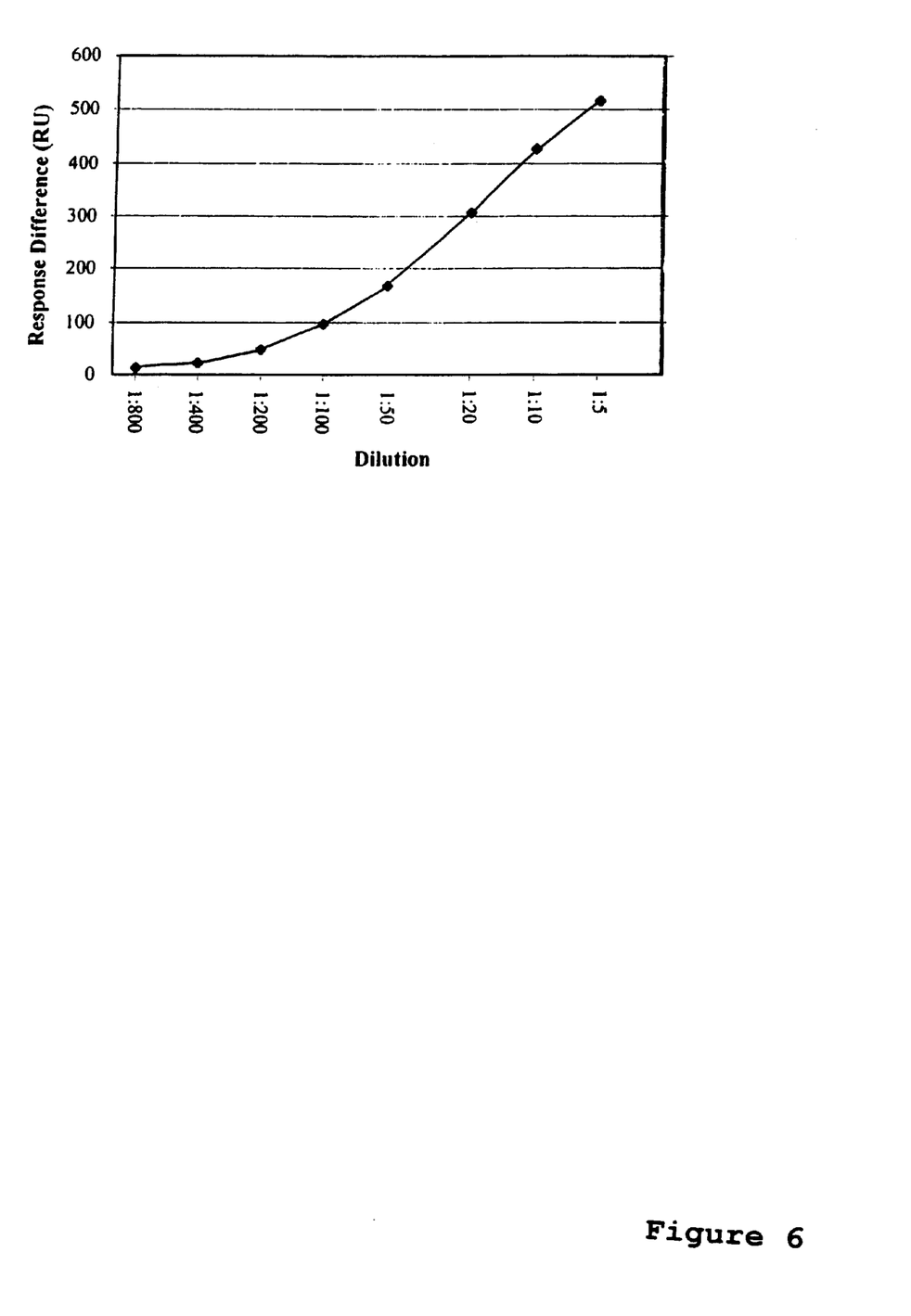
FIG. 6. Linearity of the assay was examined with serial dilutions of a serum sample in HBS-N buffer containing 1 mg/mL carboxymethyl dextran.

Linearity of the assay was tested by analyzing serial dilutions (1:5 to 1:800) of a representative serum sample (no. 2) from a patient with MMN (FIG. 5). The plot of response as a function of dilution demonstrated linearity at 1:50 and higher dilutions ($r^2$=0.9941) (FIG. 6). At higher concentrations, the curve became logarithmic, such that the plot of response as a function of log dilution yielded linearity between 1:5 and 1:100 dilutions ($r^2$=0.9949). Serial dilution of other sera showed similar results.

TABLE 1

Analysis of patient sera with SPR biosensor assay and ELSIA

|  | Number of serum samples | Number positive by ELISA | Number positive by SPR biosensor assay |
|---|---|---|---|
| MMN | 8 | 4 | 5 |
| CIDP | 5 | 0 | 0 |
| ALS | 3 | 0 | 0 |
| Anti-MAG Neuropathy | 3 | 0 | 0 |
| GBS | 2 | 1 | 1 |
| Normal | 5 | 0 | 0 |

Materials and Methods

Serum Samples. Serum samples were obtained from 21 patients: eight with multifocal motor neuropathy (MMN), five with chronic inflammatory demyelinating polyneuropathy (CIDP), three with amyotrophic lateral sclerosis (ALS), three with demyelinating neuropathy associated with anti-myelin-associated glycoprotein (anti-MAG) antibodies, and two with Guillian-Barré syndrome (GBS). One of the GBS patients was diagnosed with the Miller Fisher variant, with antibodies against GQ1b ganglioside. Criteria for patient classification have previously been described.[2,13-15] In addition, sera from five normal subjects were evaluated as controls. All patient sera were stored at −20° C.

Figure 1:
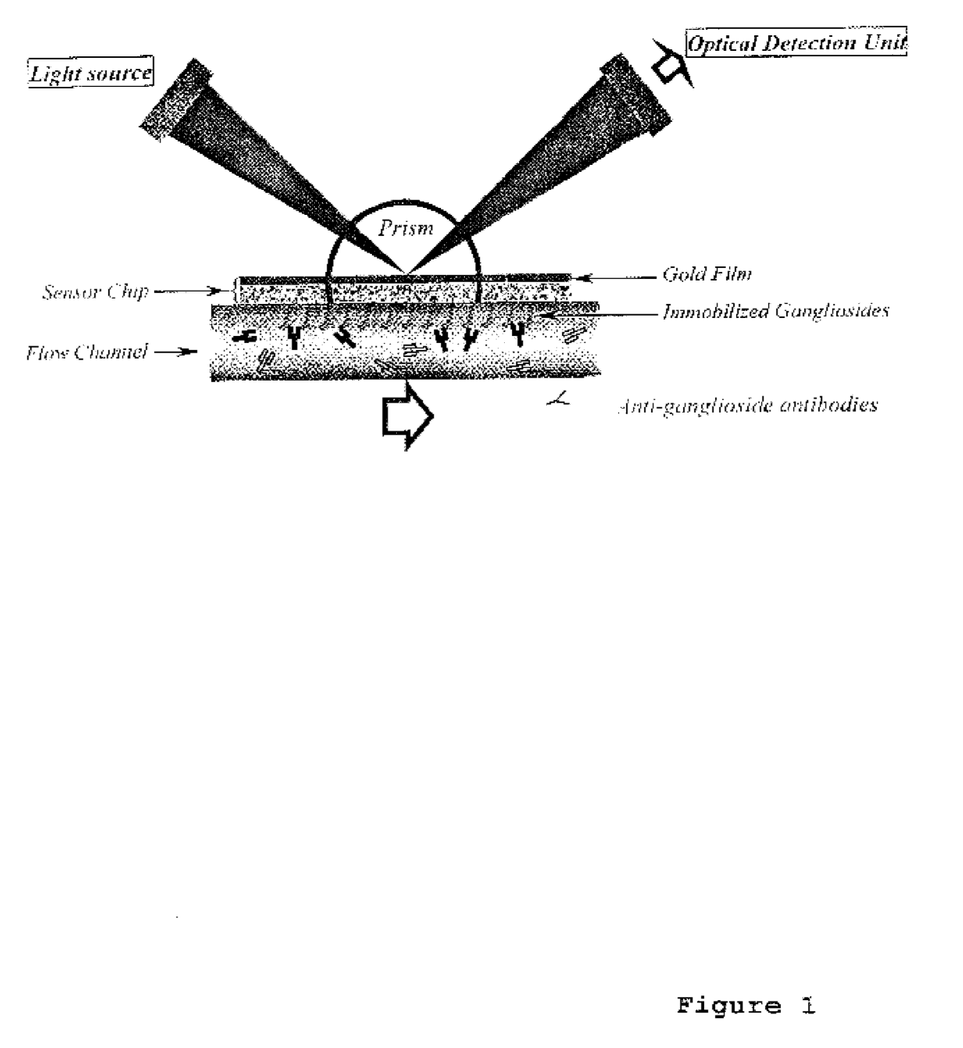
FIG. 1. Schematic representation of a surface plasmon resonance biosensor, which is based on the phenomenon of total internal reflection of light. As anti-GM1 antibodies bind the ganglioside-coated sensor chip, the resulting changes in the refractive index of the solution in contact with the chip can be detected by monitoring the change in SPR angle.

Instrument. Binding of antibodies to gangliosides was measured with a BIAcore X instrument (Biacore, Uppsala, Sweden). The system was comprised of a detector, a sensor chip for ligand immobilization, and a sample delivery unit. It utilized surface plasmon resonance, based on the optical phenomenon of total internal reflection of light, to monitor changes in refractive index at the surface of the chip, which could be visualized in the form of sensorgrams (FIG. 1).

Sensor Chip. A B1 Pioneer sensor chip (Biacore, Uppsala, Sweden) was used in the assay. The chip was composed of a glass slide with a gold film covalently linked to a methyl dextran layer containing a low degree of carboxylation. When the microfluidic cartridge of the instrument was docked against the sensor chip, two flow cells were formed, each of which could be coated with a different antigen.

Immobilization of Gangliosides. Gangliosides GM1 and GM2 (Sigma Chemicals, St. Louis, Mo.) were used as active and control antigens respectively in the immunoassay. The ganglioside GM2 was chosen as control because it is one of the least reactive gangliosides and reported cases of the presence of anti-GM2 antibodies in neuropathy patients have been fewer than those for other commercially available gangliosides. Immobilization was performed by adsorption, with the sensor chip in the instrument. A 250 µg/mL solution of GM1 was prepared by combining 20 µL of a 1 mg/mL stock solution of the ganglioside in ethanol with 60 µL of HBS-N buffer [10 mM N-(2-hydroxyethyl)piperazine-N'-(2-ethanesulfonic acid) (HEPES) buffer (pH 7.4), containing 150 mM NaCl]. Immobilization of the ganglioside was initiated by introduction of 45 µL of this solution into one of the flow cells of the sensor chip at 5 µL/min. Ganglioside GM2 was immobilized on the second flow cell in the same manner. The sensor chip was incubated at 4° C. for 48 hours, allowing the immobilized molecules to equilibrate, after which the flow cells were coated a second time as before with GM1 and GM2. Approximately 200 RU of each ganglioside was coated onto the flow cells.

SPR Analysis of Sera. All specimens were diluted 1:10 with HBS-N buffer containing 1 mg/mL carboxymethyl dextran (Fluka, Milwaukee, Wis.). The carboxymethyl dextran was used to reduce nonspecific binding. Samples were injected in triplicates at 25 µL/min for 1 minute using multi-channel detection. The samples were exposed to both active and control surfaces. Interaction of sample with each of the two ganglioside-coated surfaces of the sensor chip was monitored as a separate sensorgram. The response was measured in resonance units (RU). Presence of anti-GM1 antibodies in samples was verified by subtraction of the GM2 surface sensorgram from the GM1 surface sensorgram (FIG. 2).

Positive binding of antibodies to the GM1-coated surface indicated the presence of significant levels of anti-GM1 antibodies in the serum. Negative binding was considered to indicate the absence of detectable quantities of anti-GM1 antibodies. Final measurements were taken at 20 seconds after the end of each injection. After each measurement, the surface was regenerated with one to three 13 µL injections of 5 to 20 mM NaOH at 25 µL/min, depending on the level of antibody binding. The existence of a linear range with respect to response and antibody concentration was investigated by duplicate analysis of serially diluted samples with high levels of anti-GM1 antibodies.

Possibility of immunoglobulin class identification and signal enhancement with a secondary antibody was investigated using goat anti-human IgG and goat anti-human IgM antibodies (Sigma Chemicals, St. Louis, Mo.). Sample injection was followed by injection of a 0.5 or 0.1 mg/mL solution of the secondary antibody in HBS-N buffer containing 1 mg/mL carboxymethyl dextran.

Enzyme-Linked Immunosorbent Assay (ELISA). The presence of anti-GM1 antibodies in sera was also measured by the enzyme-linked immunosorbent assay, following previously described procedure,[3] with some modification. Wells in 96-well round-bottom polystyrene microtiter plates (Becton Dickinson, Franklin Lakes, N.J.) were coated with 0.5 ?g of GM1 in 100 µL of methanol. Wells to which only methanol was added were used as controls. After the evaporation of methanol, all wells were blocked by incubation with 300 µL of 1% bovine serum albumin (BSA) in 10 mM phosphate-buffered saline (150 mM NaCl, pH 7.4) (PBS) for 4 hours at 4° C. Wells were washed with the BSA/PBS solution, and 100 µL of serum serially diluted in the BSA/PBS solution was added to the wells. The plates were incubated at 4° C. overnight. Plates were washed as before, followed by the addition of 100 µL of peroxidase-conjugated goat anti-human IgM or IgG secondary antibody (ICN Biomedicals, Costa Mesa, Calif.) after dilution in BSA/PBS solution (a final concentration of 2.14 µg/mL) to each well, and incubation for 2 hours at 4° C. Plates were washed again and 100 µL of developing solution comprised of 27 mM citric acid, 50 mM $Na_2HPO_4$, 5.5 mM o-phenylenediamine, and 0.01% $H_2O_2$ (pH 5–5.5) was added to each well. The plates were incubated at room temperature for 30 minutes before measuring absorbance at 450 nm. The titer for each specimen was assigned as the highest dilution at which the absorbance reading was 0.1 units greater than in the corresponding control wells. Sera with titers of 800 or below were considered to be negative for the presence of clinically significant amounts of anti-GM1 antibodies, as such titers are also seen in normal subjects.

Discussion

This invention provides an SPR-based biosensor for the detection and measurement of antibodies in human serum. Presence of anti-GM1 antibodies was detected and visualized in the form of sensorgrams, using surface plasmon resonance. Interaction and specific binding of serum antibodies to the GM1-coated sensor surface were characterized by a positive response after subtraction of control sensorgram from the GM1 sensorgram. A negative response was indicative of absence of anti-GM1 antibodies in the sample. The biosensor assay was also capable of identifying antibody isotype by following sample injection with the introduction of a secondary antibody.

Assay reproducibility was evaluated by triplicate analysis of all samples. The assay exhibited high reproducibility, with standard deviations of triplicate results less than 7.1% of the mean values. Results of sample positivity or negativity were not altered in any of the repeat measurements. With the regeneration conditions used in this study, the coated sensor chip surface was stable for up to approximately 90 injections.

The biosensor immunoassay appeared to be specific for MMN and GBS patients with antibodies against GM1, as none of the other patients or normal subjects exhibited positive results. Three specimens with elevated levels of serum IgM and increased titers of anti-MAG antibodies, as well as a specimen from a patient with the Miller Fisher variant of GBS and increased titer of anti-GQ1b antibodies, tested negative for reactivity to GM1 with the biosensor assay.

With regard to sensitivity, the new assay exhibited similar results when compared to the ELISA system. It gave positive results in all four of the eight patients with MMN and elevated anti-GM1 antibodies as determined by ELISA, with titers ranging between 1,600 and 51,200. One other patient with MMN was positive by the new assay but negative by ELISA, with a titer of 800. The three remaining patients with MMN were negative for anti-GM1 antibodies by both the SPR biosensor and ELISA systems. Furthermore, the biosensor assay was capable of distinguishing between sera from patients 2 and 7 with equal antibody titers. Although both had a titer of 6,400, as determined by ELISA, the SPR assay yielded responses of 425.9 RU and 243.5 RU. This may be due to the fact that in contrast with the ELISA system, where information is provided in the form of antibody titers which are the result of analysis of serially diluted samples, the SPR biosensor assay yields data directly representative of serum antibody concentration and affinity in equally diluted sera. To be able to differentiate between the above two samples by the ELISA system with accuracy equivalent to that of the biosensor assay, significantly smaller dilutions would be necessary.

Furthermore, in comparison with ELISA, the biosensor assay was performed under more physiologic elements of temperature and concentration, and the process of incubation was eliminated. Therefore, the antibody-antigen interaction, as analyzed by the biosensor assay, is more representative of that in the human body than ELISA.

With the small number of samples analyzed, the assay showed good specificity and sensitivity. The new biosensor assay is fast, with substantially reduced sample preparation when compared to ELISA. Unlike ELISA, which is tedious and time-consuming, the biosensor assay revealed here can be completed in minutes and can be used as a rapid screening procedure for the presence of anti-GM1 antibodies. It can help in patient diagnosis as well as in accurate monitoring of patient serum antibody levels in response to treatment. In addition to testing for antibodies to GM1, the SPR biosensor immunoassay can be used in detecting antibody reactivities to other individual gangliosides, or ganglioside mixtures, by replacing the GM1 coating of the sensor chip with other antigens.

REFERENCES

1. Pestronk A, Cornblath D R, Ilyas A A, et al. A treatable multifocal motor neuropathy with antibodies to GM1 ganglioside. Ann Neurol 1988;24:73–78.
2. Kinsella L J, Lange D J, Trojaborg W, Sadiq S A, Younger D S, Latov N. Clinical and electrophysiologic correlates of elevated anti-GM1 antibody titers. Neurology 1994;44:1278–1282.
3. Sadiq S A, Thomas F P, Kilidireas K, et al. The spectrum of neurologic disease associated with anti-GM1 antibodies. Neurology 1990;40:1067–1072.
4. Kissel J T. Autoantibody testing in the evaluation of peripheral neuropathy. Semin Neurol 1998;18:83–94.
5. Asbury A K. New concepts of Guillian-Barré syndrome. J Child Neurol 2000;15:183–191.
6. Pestronk A. Motor neuropathies, motor neuron disorders, and antiglycolipid antibodies. Muscle Nerve 1991;14:927–936.
7. Marcus D M, Latov N, Hsi B P, Gillard B K. Measurement and significance of antibodies against GM1 ganglioside. Report of a workshop, Apr. 18, 1989, Chicago, Ill., USA. J Neuroimmunol 1989;25:255–259.
8. Pestronk A. Testing for serum IgM binding to GM1 ganglioside in clinical practice. Neurology 2000;54:2353–2358.
9. Carpo M, Allaria S, Scarlato G, Nobile-Orazio E. Marginally improved detection of GM1 antibodies by Covalink ELISA in multifocal motor neuropathy. Neurology 1999;53:2206–2207.
10. Holloway R G, Feasby T E. To test or not to test? That is the question. Neurology 1999;53:1905–1907.
11. Malmqvist M. Biacore: an affinity biosensor system for characterization of biomolecular interactions. Biochem Soc Trans 1999;27:335–340.
12. Fagerstam L G, Forstell-Karlsson A, Karlsson R, Presson B, Ronberg I. Biospecific interaction analysis using surface plasmon resonance detection applied to kinetic, binding site and concentration analysis. J Chromatography 1992;597:397–410.
13. Briani C, Brannagan T H $3^{rd}$, Trojaborg W, Latov N, Chronic inflammatory demyelinating polyneuropathy. Neuromuscul Disord 1996;6:311–325.
14. Van den Berg L, Hays A P, Nobile-Orazio E, et al. Anti-MAG and anti-SGPG antibodies in neuropathy. Muscle Nerve 1996;19:637–643.
15. Asbury A K, Cornblath D R. Assessment of current diagnostic criteria for Guillian-Barré syndrome. Ann Neurol 1990;27:S21–S24.

What is claimed is:

1. A method of detecting antibodies in a blood or blood derivative solution comprising:
    a) contacting the blood or blood derivative solution with a ganglioside-coated surface of a sensor chip under conditions that permit the antibodies to bind to the ganglioside coating;
    b) detecting the change in surface plasmon resonance signal of the sensor chip resulting from the antibodies binding to the ganglioside coating.
2. The method of claim 1, wherein the antigen is an anti-ganglioside antibody.
3. The method of claim 1, wherein a control surface plasmon resonance value is subtracted from the surface plasmon resonance signal.
4. The method of claim 3, wherein the control surface plasmon resonance value comprises the signal detected from the surface of the sensor chip coated with a selected control antigen, wherein the chip is also alternatively exposed to the solution being evaluated for anti-antigen antibodies.
5. The method of claim 4, wherein the control antigen is Ganglioside GM2.
6. The method of claim 1, wherein the surface plasmon resonance signal is detected from the surface of the sensor chip coated with ganglioside GM1.

7. The method of claim 1, wherein the sensor chip comprises a glass slide coated with a gold film covalently linked to a methyl dextran layer.

8. The method of claim 1, wherein the surface plasmon resonance signal is detected using an optical detector.

9. The method of claim 1, wherein the solution is human sera.

10. A method of claim 1, wherein the surface plasmon resonance signal is increased by washing the solution from the surface of the sensor chip and applying a second solution containing a secondary antibody to the surface.

11. A method of determining whether a subject is suffering from a neurological disease comprising:

a) contacting the solution with a sensor chip comprising a ganglioside coated surface under conditions that permit anti-ganglioside antibodies to bind to the ganglioside coating and the sensor chip to emit a surface plasmon resonance signal; and b) detecting a change in the surface plasmon resonance signal emitted by the sensor chip so as to thereby detect the binding of the antibodies to the ganglioside coating, wherein detection of the change in surface plasmon resonance signal indicates the subject is suffering from the neurological disease.

12. The method of claim 11, wherein the disease is Guillian-Barré syndrome, motor neuropathy, peripheral neuropathy or an autoimmune neuropathy.

* * * * *